US008377905B2

(12) United States Patent
Watanabe et al.

(10) Patent No.: US 8,377,905 B2
(45) Date of Patent: Feb. 19, 2013

(54) STABLE CRYSTAL OF 1-(2'-CYANO-2'-DEOXY-β-D-ARABINOFURANOSYL) CYTOSINE MONOHYDROCHLORIDE

(75) Inventors: Shotaro Watanabe, Kodama-gun (JP); Takahiro Hatakeyama, Kodama-gun (JP)

(73) Assignee: Delta-Fly Pharma, Inc., Tokushima-shi (JP)

( * ) Notice: Subject to any disclaimer, the term of this patent is extended or adjusted under 35 U.S.C. 154(b) by 0 days.

(21) Appl. No.: 13/264,111

(22) PCT Filed: May 14, 2010

(86) PCT No.: PCT/JP2010/003261
§ 371 (c)(1),
(2), (4) Date: Oct. 12, 2011

(87) PCT Pub. No.: WO2010/131475
PCT Pub. Date: Nov. 18, 2010

(65) Prior Publication Data
US 2012/0029182 A1 Feb. 2, 2012

(30) Foreign Application Priority Data

May 15, 2009 (JP) .................................. 2009-118726

(51) Int. Cl.
| | | |
|---|---|---|
| A01N 43/04 | (2006.01) | |
| A61K 31/70 | (2006.01) | |
| C07H 19/00 | (2006.01) | |
| C07H 19/048 | (2006.01) | |
| C07H 19/06 | (2006.01) | |

(52) U.S. Cl. ........ 514/49; 536/28.1; 536/28.4; 536/28.5
(58) Field of Classification Search ........................ None
See application file for complete search history.

(56) References Cited

U.S. PATENT DOCUMENTS 5,654,420 A * 8/1997 Matsuda et al. ............. 536/27.4

FOREIGN PATENT DOCUMENTS

EP 0535231 4/1993

OTHER PUBLICATIONS

Azuma, A., et al., "Nucleosides and nucleotides. 141. Chemical Stability of a New Antitumor Nucleoside, 2'-C-Cyano-2'-deoxy-1-β-D-*arabino*-pentofuranosylcytosine in Alkaline Medium: Formation of 2'-C-Cyano-2'-deoxy-1-β-D-*ribo*-pentofuranosylcytosine and Its Antitumor Activity[1]," Journal of Medicinal Chemistry, vol. 38, No. 17, pp. 3391-3397, (1995).
Azuma, A., et al., "Nucleosides and Nucleotides. 122. 2'-C-Cyano-2'-deoxy-1-β-D-arabinofuranosylcytosine and Its Derivatives. A New Class of Nucleoside with a Broad Antitumor Spectrum[1]," Journal of Medicinal Chemistry, vol. 36, No. 26, pp. 4183-4189, (1993).
Hirayama, N., "Methods for crystallization of drugs," Handbook for Manufacture of Crystals of Organic Compound, Principle and Know-How, pp. 57-62 & pp. 78-81, (Jul. 25, 2008) (with English translation).
Matsuda, A., et al., "Synthesis of a new potent antitumor nucleoside, 2'-C-cyano-2'-deoxy-1-β-D-arabinofuranosylcytosine," Nucleic Acids Research, Symposium Series No. 22, pp. 51-52, (1990).
"Nucleosides and Nucleotides. 100. 2'-C-Cyano-2'-deoxy-1-β-D-arabinofuranosylcytosine (CNDAC): Design of a Potential Mechanism-Based DNA-Strand-Breaking Antineoplastic Nucleoside[1]," Journal of Medicinal Chemistry, vol. 34, No. 9, pp. 2917-2919, (1991).
International Search Report issued Jul. 6, 2010 in PCT/JP10/003261 filed May 14, 2010.

* cited by examiner

*Primary Examiner* — Traviss C McIntosh, III
(74) *Attorney, Agent, or Firm* — Oblon, Spivak, McClelland, Maier & Neustadt, L.L.P.

(57) ABSTRACT

Disclosed is a stable crystal of 1-(2'-cyano-2'-deoxy-β-D-arabinofuranosyl)cytosine monohydrochloride. There is provided a crystal of 1-(2'-cyano-2'-deoxy-β-D-arabinofuranosyl)cytosine monohydrochloride having characteristic peaks at 13.7°, 15.7°, 16.0°, 18.6°, 20.3°, and 22.7° as diffraction angles (2θ±0.1°) measured by powder X-ray diffraction, and having a melting point of 192° C. to 197° C.

4 Claims, 3 Drawing Sheets

STABLE CRYSTAL OF 1-(2'-CYANO-2'-DEOXY-β-D-ARABINOFURANOSYL) CYTOSINE MONOHYDROCHLORIDE

FIELD OF THE INVENTION

The subject invention relates to novel stable crystals of 1-(2'-cyano-2'-deoxy-β-D-arabinofuranosyl)cytosine monohydrochloride, which are useful as a medicine showing an excellent anti-tumor activity, and a pharmaceutical composition containing the same.

BACKGROUND OF THE INVENTION

In general, when a compound is used as an effective active ingredient of a pharmaceutical product, the compound is required to be chemically and physically stabile so as to maintain a quality stably, and/or to facilitate storage management. Therefore, the resulting compound is preferably in the form of a stable crystal, and usually, there are many instances in which ultrastable crystals are selected as the drug substances for pharmaceutical products.

However, Patent Document 1, Non-Patent Document 1, and Non-Patent Document 2 describe that 1-(2'-cyano-2'-deoxy-β-D-arabinofuranosyl)cytosine monohydrochloride, which is a pyrimidine nucleoside derivative, represented by the following formula (1):

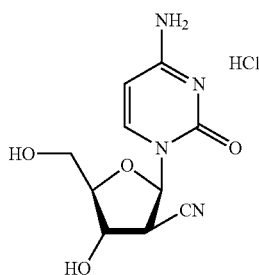

(1)

shows an in vitro suppressive effect for proliferation of human or mouse tumor cells, and also shows an excellent anti-tumor activity in vivo.

Methods for producing the compound have been reported, for example, a method of dissolving 1-(2'-cyano-2'-deoxy-β-D-arabinofuranosyl)-$N^4$-acetylcytosine represented by the following formula (2):

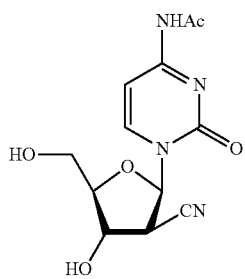

(2)

in a methanol solution of hydrochloric acid, allowing the compound to react while stirring at room temperature, and after completion of the reaction, crystallizing the product from ethanol and ether (Non-Patent Documents 1 and 2); and a method of heating the compound represented by the above formula (2) to reflux in acetic acid to thereby subject the compound to de-N-acetylation, subsequently obtaining 1-(2'-cyano-2'-deoxy-β-D-arabinofuranosyl)cytosine represented by the following formula (3):

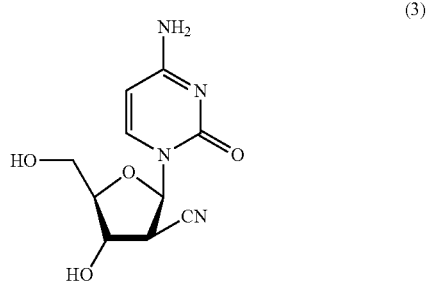

(3)

by silica gel column chromatography, dissolving the compound in a methanol solution of hydrochloric acid, allowing the compound to react while stirring at room temperature, and after completion of the reaction, crystallizing the product from ethanol and ether (Patent Document 1).

The crystal obtainable by these methods was thought to be a ½ ethanolate at the time when the document was reported, and the melting point of the crystal was considered to be 175° C. to 176° C. (Patent Document 1 and Non-Patent Documents 1 and 2). However, other than this melting point, no specific reports with regard to the crystal polymorphism or stability have been reported.

PATENT DOCUMENT

Patent Document 1: JP-B-2559917 (JP-A-4-235182)

NON-PATENT DOCUMENT

Non-Patent Document 1: Journal of Medicinal Chemistry, Vol. 34, 2917 to 2919 (1991)
Non-Patent Document 2: Journal of Medicinal Chemistry, Vol. 36, 4183 to 4189 (1993)

SUMMARY OF THE INVENTION

Problem to be Solved by the Invention

The object of the subject invention is to provide stable crystals of a compound that is useful as an anti-tumor agent.

Means for Solving the Problem

The inventors of the subject invention aimed to obtain a stable crystal of 1-(2'-cyano-2'-deoxy-β-D-arabinofuranosyl)cytosine monohydrochloride, and they first attempted to obtain a crystal of ½ ethanolate having a melting point of 175° C. to 176° C. by the known methods described in Patent Document 1 and Non-Patent Documents 1 and 2.

However, unexpectedly, the inventors of the subject invention could not reproduce the crystal of ½ ethanolate having a melting point of 175° C. to 176° C. described in the document (hereinafter, also referred to as "crystal in known document") in an experiment intended to reproduce the known methods described above.

Furthermore, the inventors of the subject invention strenuously conducted the experiment in order to obtain the crystal of ½ ethanolate having a melting point of 175° C. to 176° C., while taking into consideration of various general conditions for crystal production (see International Journal of Pharmaceutics, Vol. 60, 11 to 26 (1990), and the like). However, the inventors eventually could not reproduce the crystal described in known document.

In that case, it is contemplated that a crystal, that is not obtainable even when such various production conditions are taken into consideration, cannot be regarded as a preferable crystal that can be produced and supplied stably in industrial scale. The reason may be that the crystal obtained at that time may be a crystalline polymorph. When the presence of a crystalline polymorph in a drug substance for pharmaceutical products is confirmed, it is usually no longer easy to stably produce a single crystal or a mixed type crystal in which the content ratio is constantly maintained, and therefore, an extensive investigation is required.

However, there have been some reports published in the past, reporting that a crystal that could be conventionally obtained suddenly cannot be obtained by the techniques of the related art ever since a certain time. For example, in the case of Ritonavir, an anti-human immunodeficiency virus (HIV) drug, a document reports that due to the sudden appearance of Form II (a stable crystal), the traditionally obtained Form I crystal can no longer be obtained by the traditional production method (Organic Process Research and Development, Vol. 4, 413 to 417 (2000)). Also in the case of a compound that has been developed as a cephem-based antibiotic substance, a document reports that due to the sudden appearance of γ-crystal (a stable crystal), the traditionally obtained α-crystal can no longer be obtained by the traditional production method (Bunri Gijutsu (Separation Technology), Vol. 33, 379 to 385 (2003)). Even in the case of a compound that has been developed as a HIV-1 reverse transcriptase inhibitor, a document reports that due to the sudden appearance of Form III crystal (a stable crystal), the traditionally obtained Form I crystal can no longer be obtained by the traditional production method (Organic Process Research and Development, Vol. 9, 933 to 942 (2005)).

According to these findings, it is contemplated that the crystals in prior art document obtainable at the relevant time could not be obtained because the crystal in the prior art document was inferior to the crystal of the subject invention in terms of stability. It is also contemplated that, even if the crystal in prior art document were temporarily generated in the reaction system, the crystal in the prior art document immediately varies to a stable crystal through crystalline transition, and consequently, the crystal in prior art document could not be obtained.

During investigation for the subject invention, the inventors of the subject invention found that, as shown in Examples described below, crystals which do not contain ethanol and have a melting point 15° C. to 20° C. higher than the melting point of 175° C. to 176° C. of the conventionally known crystal (hereinafter, also referred to as "crystals of the subject invention") are obtained, and that since the melting point of a crystal having excellent stability (stable crystal) is generally higher than the melting point of an unstable crystal (metastable crystal), the crystals of the subject invention are stable crystals. Accordingly, the inventors have completed the subject invention.

The subject invention relates to the following items (1) to (4).

(1) A crystal of 1-(2'-cyano-2'-deoxy-β-D-arabinofuranosyl)cytosine monohydrochloride having characteristic peaks at 13.7°, 15.7°, 16.0°, 18.6°, 20.3°, and 22.7° as diffraction angles (2θ±0.1°) measured by powder X-ray diffraction, and having a melting point of 192° C. to 197° C.

(2) A crystal of 1-(2'-cyano-2'-deoxy-β-D-arabinofuranosyl)cytosine monohydrochloride having characteristic peaks at 6.4°, 12.6°, 17.3°, and 21.7° as diffraction angles (2θ±0.1°) measured by powder X-ray diffraction, and having a melting point of 192° C. to 197° C.

(3) A pharmaceutical composition comprising the crystal according to (1) or (2).

(4) An anti-tumor agent comprising the crystal according to (1) or (2).

Effect of the Invention

Since the crystals of 1-(2'-cyano-2'-deoxy-β-D-arabinofuranosyl)cytosine monohydrochloride of the subject invention show excellent physical stability and/or chemical stability, the crystals are excellent as compared with other amorphous form, other crystal forms or the like of 1-(2'-cyano-2'-deoxy-β-D-arabinofuranosyl)cytosine from the viewpoints of, for example, storage stability, purity, usability (lower hygroscopicity) and/or product manageability, and from the viewpoint that the crystals have an excellent anti-tumor effect and are therefore useful as anti-tumor agents. Thus, the crystals of the subject invention are useful as a medicine.

DETAILED DESCRIPTION OF THE INVENTION

Figure 1:
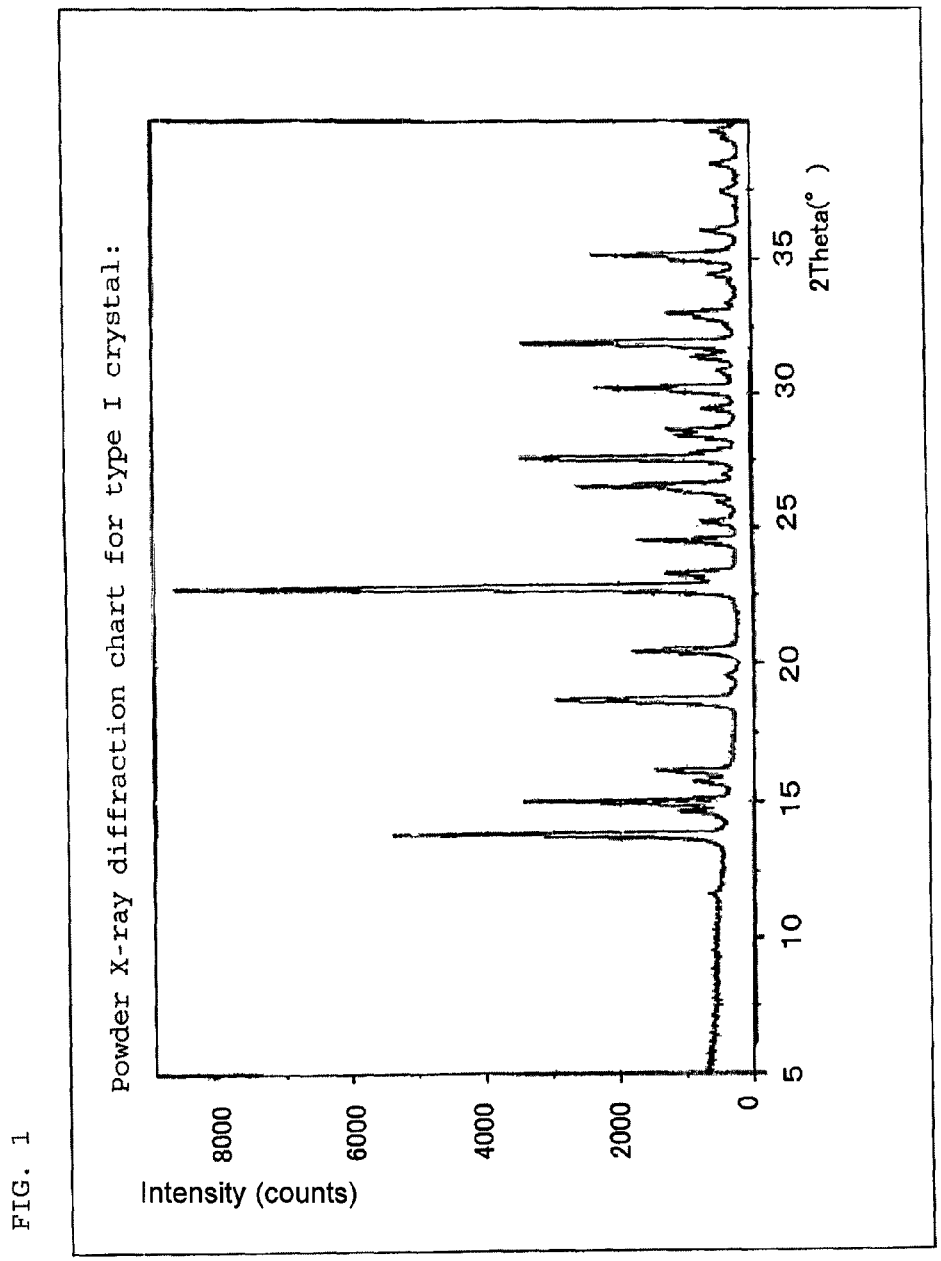
FIG. 1 is a powder X-ray diffraction chart of the type I crystal.

The crystals of the subject invention, particularly three types of crystals, such a type I crystal, a type II crystal and a type III crystal, can be respectively obtained as single crystals by crystallization or recrystallization from a solution containing 1-(2'-cyano-2'-deoxy-β-D-arabinofuranosyl)cytosine monohydrochloride represented by the above formula (1) (hereinafter, also referred to as "compound (1)").

Furthermore, the compound (1) may not be in a crystalline form, also the compound (1) may be in a crystalline form. If the compound (1) is in a crystalline form, for example, the type I crystal may be separated by using the type II crystal as a raw material, or the type I crystal may be separated by using the type III crystal as a raw material.

The 1-(2'-cyano-2'-deoxy-β-D-arabinofuranosylcytosine monohydrochloride (compound (1)) used in the subject invention can be obtained by an organic chemical synthesis method by using 1-(2'-cyano-2'-deoxy-β-D-arabinofuranosyl)-$N^4$-acetylcytosine represented by the above formula (2) (hereinafter, also referred to as "compound (2)"), or 1-(2'-cyano-2'-deoxy-β-D-arabinofuranosyl)cytosine represented by the above formula (3) (hereinafter, also referred to as "compound (3)") as a raw material. For example, the compound (1) can be obtained by subjecting the compound (2) to de-N-acetylation and addition of hydrochloric acid, or by subjecting the compound (3) to addition of hydrochloric acid.

More specific examples of the method for obtaining the compound (1) include, for example, a method of treating the compound (2) with an acid to obtain the compound (3), and subjecting this compound to addition of hydrochloric acid to obtain the compound (1); a method of subjecting the compound (2) to an acid treatment and addition of hydrochloric acid in one step by using a hydrochloric acid-methanol solution, and thereby obtaining the compound (1).

Among these, from the viewpoints of improving operating efficiency or yield, it is preferable to carry out an acid treatment and hydrochloric acid addition in one step, and the reaction condition of this case is preferably using 1 to 20 mL of a 0.5% to 3% hydrochloric acid-methanol solution relative to 100 mg of the compound (2), and stirring the mixture at about 10° C. to 40° C. (preferably, room temperature) for 0.5 to 3 hours (preferably 1±0.25 hours).

The compounds (2) and (3) can be produced by the production methods described in the above mentioned Patent Document 1 and Non-Patent Documents 1 and 2.

Furthermore, examples of the acid that is used in the acid treatment include inorganic acids such as sulfuric acid and hydrochloric acid; and organic acids such as acetic acid and trifluoroacetic acid. These acids may be used alone or as mixtures of two or more kinds.

The method of deposition of the crystals of the subject invention is not particularly limited, including, for example, a method of dissolving the compound (1) in a solvent that dissolves the compound (1) under heating (hereinafter, also referred to as "dissolving solvent"), allowing the solution in which the compound (1) is dissolved to stand still or cooling the solution with a cooling means, and thereby depositing the crystal; a method of deposition of the crystal from the solution in which the compound (1) is dissolved (hereinafter, also referred to as "dissolved solution"), using a solvent having low solubility for the compound (1) (hereinafter, also referred to as "low-solubility solvent"). Among these, the method of deposition of the crystal from the dissolving solution using a low-solubility solvent is preferred. An example of this method may be, for example, a method of adding the dissolved solution to a pre-cooled low-solubility solvent, and thereby depositing the crystal.

The solvent used in the process of deposition of the crystal is not particularly limited, such a solvent including, for example, water; alcohols such as methanol, ethanol, and isopropanol; ketones such as acetone and methyl ethyl ketone; ethers such as diethyl ether, diisopropyl ether, and t-butyl methyl ether. These solvents can be used alone or as mixtures of plural solvents.

The dissolving solvent is preferably a solvent that is capable of dissolving the compound (1) under heating, and specifically, alcohols are more preferred in view of stability. Among these, an alcohol having 1 to 5 carbon atoms, particularly ethanol, is preferred. Typically, the temperature of the dissolving solvent when heating is preferably from 0° C. to the boiling point of the solvent, and more preferably from 20° C. to 40° C. The concentration of the compound (1) is not particularly limited, preferably 0.25 to 0.6 (W/V) % in the dissolved solution.

The low-solubility solvent is preferably a solvent that is capable of depositing the crystal when the solvent is added to the solution in which the compound (1) is dissolved, and then the mixture is left to stand or cooled. Specifically, ethers are preferred from the viewpoint of stability, and among these, diethyl ether is particularly preferred.

When the dissolving solution is added, the temperature of the low-solubility solvent is preferably from −40° C. to the boiling point of the solvent, more preferably from −20° C. to 20° C., and even more preferably from 0° C. to 10° C. On the other hand, the temperature of the dissolving solution, when the dissolving solution is added to the low-solubility solvent, is preferably from −20° C. to the boiling point of the solvent, more preferably from −5° C. to 45° C., and even more preferably from 0° C. to 40° C.

The amount of use of the low-solubility solvent is preferably from 0 to 1 part by volume relative to 1 part by volume of the dissolving solution.

The temperature at the time of deposition is typically preferably from −50° C. to 30° C., more preferably from −40° C. to 20° C., and even more preferably from −30° C. to 10° C. In this case, the dissolving solution or a mixed solution of the dissolving solution and the low-solubility solvent may be cooled with the cooling means. For example, adding dropwise the dissolving solution to a cooled vessel; cooling the dissolving solution or the mixed solution may be carried out. In deposition, the solution may be left to stand still, or may be stirred.

The deposited crystal can be isolated and purified from the dissolving solution or the mixed solution by, for example, known separation and purification techniques such as filtration, washing with an organic solvent, and drying under reduced pressure. Examples of the organic solvent used in the washing process include the low-solubility solvents mentioned above, and among these, the ethers described above are used with preference.

In this manner, the crystals of the subject invention, particularly the type I crystal, type II crystal, and type III crystal, can be produced.

For example, as a method for obtaining the type I crystal, it is preferable to obtain the type I crystal by dissolving under heating the compound (1) in ethanol, and then adding this solution dropwise into diethyl ether that has been cooled to 0±5° C. while stirring the mixture.

As a method for obtaining the type II crystal, it is preferable to obtain the type II crystal by dissolving under heating the compound (1) or the type I crystal in ethanol, subsequently cooling this solution to 40±5° C., and then adding diethyl ether dropwise to the solution while stirring the mixture.

Furthermore, as a method for obtaining the type III crystal, it is preferable to obtain the type III crystal by dissolving under heating the compound (1) or the type I crystal in ethanol, and then adding this solution dropwise onto a plate that has been cooled to 0±5° C.

Figure 2:
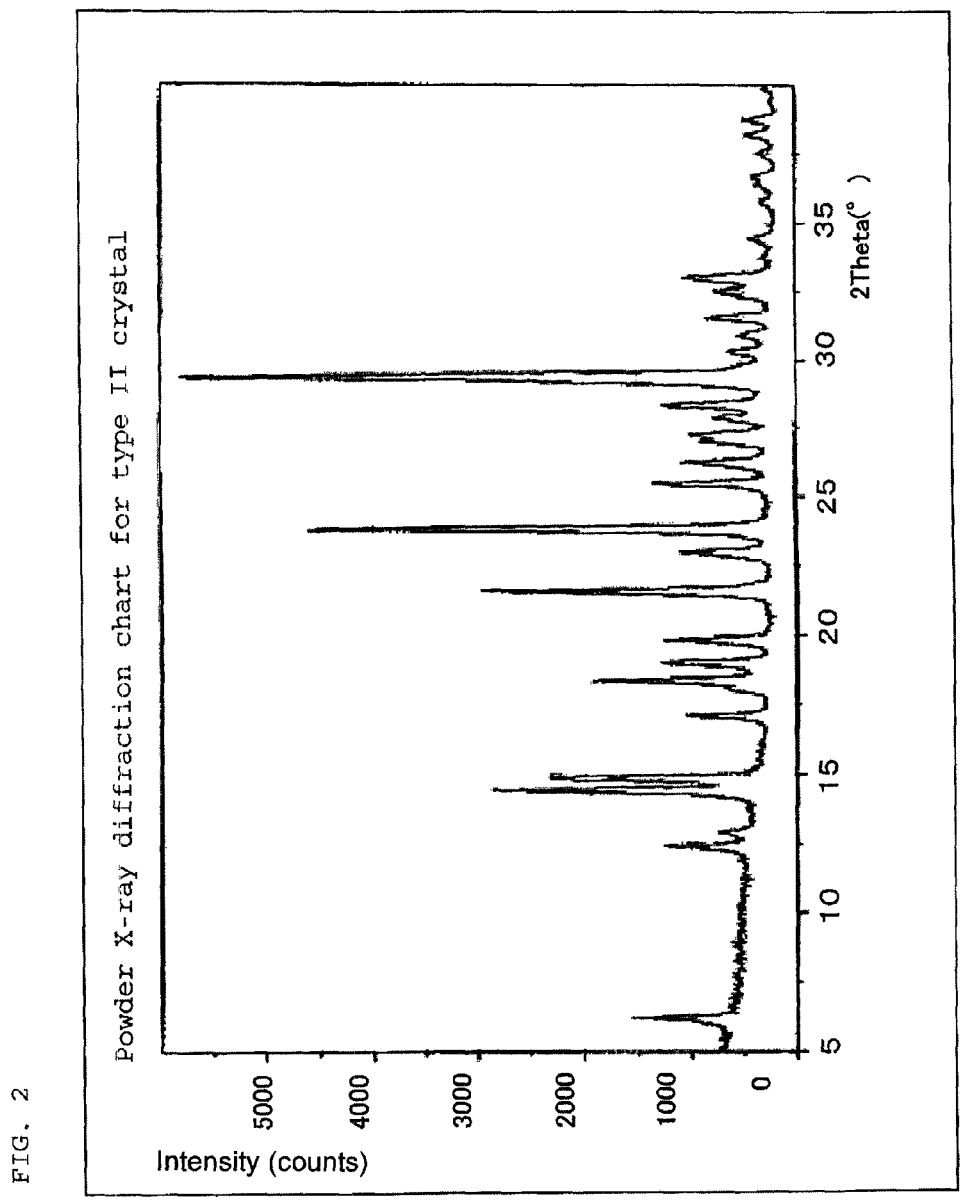
FIG. 2 is a powder X-ray diffraction chart of the type II crystal.
Figure 3:
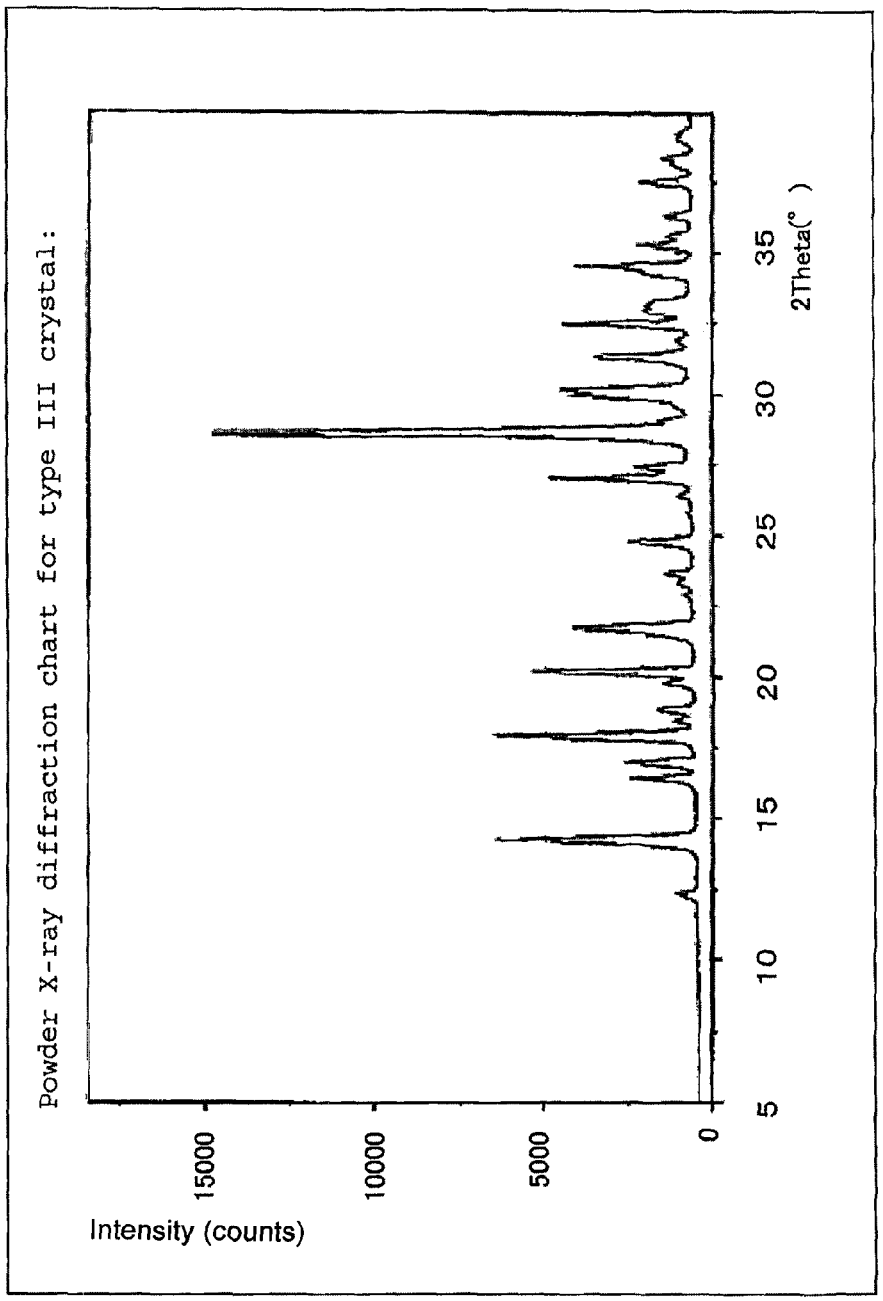
FIG. 3 is a powder X-ray diffraction chart of the type III crystal.

The melting point of the type I to III crystals of the compound (1) obtained as described above is 192° C. to 197° C., and as shown in the powder X-ray diffraction charts of FIGS. 1 to 3, the crystals are distinguished by the following characteristic diffraction peaks.

That is, as shown in FIG. 1, the powder X-ray diffraction pattern of the type I crystal exhibits characteristic peaks at around 13.7°, 15.7°, 16.0°, 18.6°, 20.3° and 22.7° as the diffraction angles (2θ±0.1°) measured by powder X-ray diffraction.

As shown in FIG. 2, the powder X-ray diffraction pattern of the type II crystal exhibits characteristic peaks at around 6.4°, 12.6°, 17.3°, and 21.7° as the diffraction angles (2θ±) 0.1° measured by powder X-ray diffraction.

Furthermore, as shown in FIG. 3, the powder X-ray diffraction pattern of the type III crystal exhibits characteristic peaks at around 14.2°, 16.4°, 17.0°, 18.0° and 20.2° as the diffraction angles (2θ±0.1°) measured by powder X-ray diffraction.

The crystals of the subject invention show high storage stability, are advantageous in terms of quality management, and also involve and excellent usability. Particularly, as shown in the Examples described below, even if the type I crystal is stored for a long time under high temperature and high humidity conditions, the content of total analogues is hardly detected, and the change of crystal form is hardly observed. Also, since the type II crystal or the type III crystal is converted to the type I crystal when the type II crystal or the type III crystal is heated at around 70° C. to 90° C. for several hours and stored at around 30° C. to 50° C. for a long time (one month) and at a humidity of 75% RH or higher, the type I crystal has superior stability as compared with the type II crystal or the type III crystal.

As is obvious from the descriptions of the Patent Document 1, since the compound (1) shows a strong anti-tumor activity, a pharmaceutical composition containing the crystals of the subject invention can be used particularly as an anti-tumor agent, and can be used for the manufacture of the same.

The purity of the crystals of the subject invention, particularly of the type I, type II and type III crystals in the respective crystal forms of the same, is preferably substantially 95% or greater, more preferably substantially 98% or greater, and even more preferably substantially 99% or greater.

The crystals of the subject invention can be processed, after being pulverized or without being pulverized, into various forms of anti-tumor agents, for example, oral preparations such as tablets, capsules, granules, fine granules, powders, and syrups; parenteral preparations such as intravenous injectable preparations, subcutaneous injectable preparations, intramuscular injectable preparations, and suppositories. The crystals of the subject invention are to be intravenously administered, and the dosage form is preferably an injectable preparation. Such an injectable preparation is desirably used as a solid injectable preparation, such as a lyophilized injectable preparation or a powder injectable preparation, which can be used by dissolving at the time of use.

The anti-tumor agent can be produced by a preparation method known to and commonly used by those ordinarily skilled in the art, by using a pharmaceutically acceptable carrier. In this case, other anti-tumor agents, for example, 5-FU, a tegafur-uracil formulation, a tegafur-gimeracil-oteracil potassium formulation, doxorubicin, epirubicin, irinotecan hydrochloride, etoposide, docetaxel, pacritaxel, cisplatin, carboplatin, oxaliplatin, krestin, lentinan, picibanil may also be used in combination.

The dosage amount of the crystals of the subject invention in case of using as an anti-tumor agent may vary depending on, for example, the symptoms of the patient to whom the anti-tumor agent is applied, the dosage form; however, in general, it is preferable to administer the anti-tumor agent once or several times a day in an amount of 2.0 to 4.0 mg/m$^2$ in terms of the crystals of the subject invention.

EXAMPLES

Hereinafter, the production method of the subject invention is specifically described by way of Examples and Reference Examples.

Reference Example 1

Synthesis of 1-(2'-cyano-2'-deoxy-β-D-arabinofuranosyl)-N$^4$-acetylcytosine

1 M of THF solution (2 mL) of tetrabutylammonium fluoride and 0.06 mL (1 mmol) of acetic acid were added to a THF (5 mL) solution of N$^4$-acetyl-2'-cyano-2'-deoxy-3',5'-O-(1,1,3,3-tetraisopropyl disiloxane-1,3-diyl)-1-β-D-arabinofuranosylcytosine (537 mg, 1 mmol), and the mixture was stirred at room temperature for 15 minutes. After the stirring, the mixture was concentrated, and the residue was purified by silica gel (11 g) column chromatography by using 8% ethanol-chloroform as a developing solvent. The concentrated residue of the target fraction was washed with hexane-diethyl ether, and thus 259 mg (yield: 88%) of the title compound was obtained as a white crystal.

Example 1

Synthesis of 1-(2'-cyano-2'-deoxy-β-D-arabinofuranosyl)cytosine monohydrochloride 1-(2'-cyano-2'-deoxy-β-D-arabinofuranosyl)-N$^4$-acetylcytosine (100 mg, 0.34 mmol) was dissolved in 1% hydrochloric acid-methanol (7.5 mL), and the mixture was stirred at room temperature (20° C. to 25° C.) for one hour. The reaction liquid was concentrated, and ethanol (10 mL) was poured into this concentrate. The mixture was co-evaporated, and thus 34 mg of the title compound was obtained (yield: 35%).

Melting point: 192° C.
Elemental Analysis:
Calculated value (as $C_{10}H_{13}ClN_4O_4$): C, 41.60; H, 4.54; N, 19.41
Found value: C, 41.45; H, 4.52; N, 19.41

Example 2

Preparation of Type I Crystal of 1-(2'-cyano-2'-deoxy-β-D-arabinofuranosyl)cytosine monohydrochloride 1-(2'-cyano-2'-deoxy-β-D-arabinofuranosylcytosine monohydrochloride (200 mg) obtained in Example 1 was heated to reflux in ethanol (34 mL) and was dissolved therein. The solution was added dropwise to diethyl ether (34 mL) that had been cooled to 0° C. The mixture was stirred for 2 hours, and then a precipitate was collected by filtration and was dried under reduced pressure at 35° C. Thus, 123 mg (yield: 62%) of the title compound was obtained as the type I crystal.

Melting point (decomposition point): 192° C. to 197° C.
Elemental Analysis:
Calculated value (as $C_{10}H_{13}ClN_4O_4$): C, 41.60; H, 4.54; N, 19.41
Found value: C, 41.64; H, 4.51; N, 19.28

FIG. 1 shows the powder X-ray diffraction chart of the type I crystal obtained herein. Characteristic peaks were recognized at around 13.7°, 15.7°, 16.0°, 18.6°, 20.3° and 22.7° as the diffraction angles (2θ±0.1°) measured by powder X-ray diffraction.

The powder X-ray diffraction data were obtained by irradiating the crystal with CuKα ray (1.541 Å) using an X-ray diffraction apparatus (trade name: PW3050, manufactured by Koninklijke Philips Electronics N.V.), and detecting the angles using a vertical goniometer.

Example 3

Preparation of II-Type Crystal of 1-(2'-cyano-2'-deoxy-β-D-arabinofuranosyl)cytosine monohydrochloride The type I crystal of 1-(2'-cyano-2'-deoxy-β-D-arabinofuranosyl)cytosine monohydrochloride (200 mg) was heated to reflux in ethanol (34 mL) and was dissolved therein, and the solution was cooled to 40° C. Subsequently, the ethanol (34 mL) in which this compound was dissolved was poured, by being added dropwise, into diethyl ether (34 mL) which was in a reflux state (reaction vessel heated to 40° C.). The mixture was stirred for one hour while refluxing, and then a precipitate generated in diethyl ether was collected by filtration and was dried under reduced pressure at 35° C. Thus, 119 mg (yield: 60%) of the title compound was obtained as the II-type crystal.

FIG. 2 shows the powder X-ray diffraction chart of the type II crystal obtained herein. This type II crystal was analyzed using a powder X-ray diffraction apparatus in the same manner as described above, and characteristic peaks were recognized at around 6.4°, 12.6°, 17.3°, and 21.7° as the diffraction angles (2θ±0.1°) measured by powder X-ray diffraction.

Melting point (decomposition point): 192° C. to 196° C.
Elemental Analysis:
Calculated value (as $C_{10}H_{13}ClN_4O_4$): C, 41.60; H, 4.54; N, 19.41
Found value: C, 41.48; H, 4.57; N, 19.14

Example 4

Preparation of Type III Crystal of 1-(2'-cyano-2'-deoxy-β-D-arabinofuranosyl)cytosine monohydrochloride The type I crystal of 1-(2'-cyano-2'-deoxy-β-D-arabinofuranosyl)cytosine monohydrochloride (200 mg) was heated to reflux in ethanol (34 mL) and was dissolved therein, and the solution thus obtained was slowly added dropwise to a vessel that had been cooled to 0° C. The solution was stirred for 2 hours, and then a precipitate was collected by filtration and was dried under reduced pressure at 35° C. Thus, 66 mg (yield: 33%) of the title compound was obtained as the type III crystal.

FIG. 3 shows the powder X-ray diffraction chart of the type III crystal obtained herein. This type III crystal was analyzed using a powder X-ray diffraction apparatus in the same manner as described above, and characteristic peaks were recognized at around 14.2°, 16.4°, 17.0°, 18.0°, and 20.2° as the diffraction angles (2θ±0.1°) measured by powder X-ray diffraction.

Melting point: 195° C.
Elemental Analysis:
Calculated value (as $C_{10}H_{13}ClN_4O_4$): C, 41.60; H, 4.54; N,
Found value: C, 41.59; H, 4.42; N, 19.29

Example 5

Stability Test

The type I and type II crystal powders were respectively spread uniformly on a glass petri dish, and an aluminum foil (or a transparent resin film, for the purpose of storage under light exposure conditions) which was appropriately perforated as vent holes therein was used as a lid, to prepare test samples. These samples were respectively stored for 30 days under four kinds of conditions such as [60° C.], [40° C./relative humidity (RH) 75%], [25° C./relative humidity (RH) 60%, light exposure 2000 lx·hr], and [25° C./relative humidity (RH) 60%, light shading], and then the samples were tested using high performance liquid chromatography (HPLC) and powder X-ray diffraction (XRD).

For powder X-ray diffraction (XRD), the analysis was carried out as described above.

For the HPLC analysis, 22.9 mg of the sample was dissolved in 10 mL of 0.01 mol/L hydrochloric acid, and then the content of analogues in the crystal was measured under the following conditions.

Column: Synergi Hydro-RP 80A Phenomenex (φ4.6 mm×25 cm, 4 μm); temperature 25° C.

Mobile phase: 2.05 g of potassium dihydrogen phosphate is dissolved in 3000 mL of water, and phosphoric acid is added to the solution to adjust the pH to 3.0. The mobile phase is prepared by adding 60 mL of methanol to 2940 mL of the solution liquid.

Flow rate: Approximately 1.0 mL/min
Detector: Ultraviolet absorptiometer (measurement wavelength 254 nm)
Standard Sample:
1-(2'-cyano-2'-deoxy-β-D-arabinofuranosyl)cytosine monohydrochloride The term "total analogues" refers to the substances detected other than 1-(2'-cyano-2'-deoxy-β-D-arabinofuranosyl)cytosine monohydrochloride), and the term "total analogues (%)" refers to the content ratio of total analogues with respect to the standard sample.

The results of this stability test are shown in Table 1.

The type I crystal and the type II crystal were both subjected to the stability test under various conditions (under the conditions of humidification and exposure). As a result, an increase in the total analogues was not recognized as presented in Table 1, and the crystals were found to be highly stable crystal forms.

Furthermore, the type II crystal was converted to the type I crystal after 30 days under the conditions of 40° C./relative humidity (RH) 75%, and the melting point and the powder X-ray diffraction chart were consistent with those obtained in Example 1. Also, the type III crystal was converted to the type I crystal when heated at 80° C. for 2 hours, and the melting point and the powder X-ray diffraction chart were consistent with those obtained in Example 1.

From these results, it was found that melting point of the type I to III crystals are 192° C. to 197° C. and involve an excellent stability. Particularly, the type I crystal was found to show superior stability as compared with the type II crystal or the type III crystal.

TABLE 1

| Storage temperature | Crystal form | Total analogues (%) | | | | Amount of increase from the initial value | Change of crystal form from the initial value |
|---|---|---|---|---|---|---|---|
| | | Storage period | | | | | |
| | | initial | 10 days | 18 days | 30 days | | |
| 60° C. | I | 0.07 | 0.06 | 0.07 | 0.07 | 0.00 | No change |
| | II | 0.06 | 0.06 | 0.07 | 0.07 | 0.01 | No change |
| 40° C./75% RH | I | 0.07 | 0.07 | 0.06 | 0.05 | −0.02 | No change |
| | II | 0.06 | 0.06 | 0.08 | 0.16 | 0.10 | Changed (II → I) |
| 25° C./60% RH/2000 lx | I | 0.07 | 0.09 | 0.09 | 0.13 | 0.06 | No change |
| | II | 0.06 | 0.15 | 0.23 | 0.38 | 0.32 | No change |
| 25° C./60% RH/Light shading | I | 0.07 | 0.07 | 0.06 | 0.07 | 0.00 | No change |
| | II | 0.06 | 0.06 | 0.07 | 0.09 | 0.03 | No change |

The invention claimed is:

1. A crystal of 1-(2'-cyano-2'-deoxy-β-D-arabinofuranosyl)cytosine monohydrochloride having characteristic peaks at 13.7°, 15.7°, 16.0°, 18.6°, 20.3°, and 22.7° as diffraction angles (2θ±0.1°) measured by powder X-ray diffraction, and having a melting point of 192° C. to 197° C.

2. A crystal of 1-(2'-cyano-2'-deoxy-β-D-arabinofuranosyl)cytosine monohydrochloride having characteristic peaks at 6.4°, 12.6°, 17.3°, and 21.7° as diffraction angles (2θ±0.1°) measured by powder X-ray diffraction, and having a melting point of 192° C. to 197° C.

3. A pharmaceutical composition comprising the crystal according to claim 1 or 2.

4. An anti-tumor agent comprising the crystal according to claim 1 or 2.

* * * * *